United States Patent [19]

Imperatori

[11] Patent Number: 5,062,994
[45] Date of Patent: Nov. 5, 1991

[54] WATER-FREE SKIN CLEANING COMPOSITION IN THE FORM OF A TABLET

[76] Inventor: Diana Imperatori, Via Melloni, 8, 20129 Milano, Italy

[21] Appl. No.: 437,363

[22] Filed: Nov. 15, 1989

[30] Foreign Application Priority Data

Nov. 22, 1988 [IT] Italy ................... 22694 A/88

[51] Int. Cl.$^5$ ............... C11D 1/88; C11D 17/00
[52] U.S. Cl. .............. 252/545; 252/DIG. 5; 252/DIG. 16; 252/547; 252/550; 252/551; 252/174.17; 252/544
[58] Field of Search ........... 252/DIG. 5, DIG. 16, 252/88, 89, 174.17, 545, 550, 551, 544

[56] References Cited

U.S. PATENT DOCUMENTS

| | | | |
|---|---|---|---|
| 4,765,922 | 8/1988 | Contamin et al. | 252/90 |
| 4,784,788 | 11/1988 | Lancz | 252/114 |
| 4,786,369 | 11/1988 | Kanfer et al. | 252/120 |
| 4,786,432 | 11/1988 | Kanfer et al. | 252/120 |
| 4,808,322 | 2/1989 | McLaughlin | 252/121 |
| 4,812,253 | 3/1989 | Small et al. | 252/132 |
| 4,885,109 | 12/1989 | Umemoto et al. | 252/174.21 |
| 4,919,838 | 4/1990 | Tibbetts et al. | 252/117 |

*Primary Examiner*—Prince Willis, Jr.
*Assistant Examiner*—J. Silbermann
*Attorney, Agent, or Firm*—Bucknam and Archer

[57] ABSTRACT

The present invention relates to a skin cleaning composition, in particualr a personal hygiene composition, comprising at least a powder cleaning substance selected from anionic, amphoteric, non-ionic, cationic cleaning materials, either individually or in mixture.

The cleaning composition is associated with at least an absorbing cooperating powder so as to provide a cleaning product having a very high skin cleaning efficiency in small doses.

1 Claim, No Drawings

WATER-FREE SKIN CLEANING COMPOSITION IN THE FORM OF A TABLET

BACKGROUND OF THE INVENTION

The present invention relates to a skin cleaning composition for personal hygiene use.

As is known, several skin cleaning compositions are available on the market, including, for example, solid paste products of different shapes usually based on alkaly substance soaps, or synthetic cleansing substances adjusted to a slightly acid pH.

These solid paste products, even if they are the most popular skin cleaning materials, are however affected by a lot of drawbacks, the most important of which is that they do not assure perfect hygiene conditions, since they are usually provided for a multiple use, that is used by a lot of persons.

Moreover the above mentioned solid paste cleaning products leave in their holders a water residue which softens the paste material. Moreover, if the holding cup has draining openings, an aqueous slurry drains on the floor or in the basin, which is rather objectable.

Other cleaning products comprise mostly dense solutions including surface-active, anionic, amphoteric, non ionic or cationic components in an aqueous solution: these products typically comprise shampoo's, bath foam compositions, personal hygiene compositions and the like.

Also these products, which contain comparatively high water amounts, however, are affected by great drawbacks, for example high shipment costs: moreover water favours the growth of fungi and bacteria and, because of this fact, preserving agents must be included in these cleaning materials, which are susceptible to locally irritate the skin.

These solution products, moreover, must be held in expensive bottles, which can involve tightness problems.

To the foregoing it is to be added that the use of these solution sking cleaning products in communities and the like is rather disavantageous, since metering devices holding these products must be periodically filled and serviced.

Yet another type of known skin cleaning products consists of the so-called emulsions or "milks" which generally comprise water-oil emulsions: these products, as it should be apparent, have the same drawbacks as the cleaning solutions and moreover a poor cleaning efficiency. Because of this fact, the use of these products is generally limited to the cleaning of the face skin.

Yet other types of skin cleaning products or compositions comprise powder or granulated materials, mainly based on anionic, amphoteric, non ionic and cationic substances.

These products, on the other hand, can be metered and supplied with great difficulties: moreover these powder products are susceptible to irritate the respiratory ducts of the users and, because of this reason, these cleaning products can not be used in communities and the like.

SUMMARY OF THE INVENTION

Accordingly, the object of the present invention is to overcome the above mentioned drawbacks of known skin cleaning products by providing a new skin cleaning product, for personal hygiene use, which can be used in a very safe and advantageous way.

Within the scope of the above, a main object of the invention is to provide such a skin cleaning product which has a very high cleaning efficiency, even in very small doses, and does not irritate the user's skin.

Another object of the invention is to provide such a skin cleaning product or composition which is specifically designed for a single use application and can be easily and quickly filled in automatic dispensing units.

According to one aspect of the present invention, the above mentioned objects, as well as other objects, which will become more apparent hereinafter, are achieved by a skin cleaning composition characterized in that said composition comprises at least a powder cleaning substance selected from anionic, amphoteric, non ionic, cationic cleaning compounds, either individually or in mixture, and an absorbing and cooperating compound.

Further characteristics and advantages of the invention will become more apparent from the following detailed description of a preferred, though not exclusive, embodiment of a composition for cleaning skin according to the invention.

More specifically, the skin cleaning composition according to the invention substantially comprises a powder skin cleaning substance selected from anionic, amphoteric, non ionic, cationic cleaning compounds, which can be used either individually or in mixture, and which are associated with a particular absorbing and cooperating powder, so as to provide a composition having a high skin cleaning efficiency.

The composition of the invention can be packaged or formed into tablets, of flexible and advantageous use, and with small doses of the individual components because of the synergistic cooperation of the cleaning substances and absorbing additive powder.

This feature, as already stated, is such to preserve the skin fat, while preventing delicate skin from being irritated.

The tablets, moreover, can be filled in suitable dispensing devices, which provide very hygienic use conditions, particularly suitable for communities and the like.

According to some preferred embodiments, the powder cleaning substances can comprise: alkylsulphates, alkylether sulphates, non ionic soaps of the alkylamide or polyoxyethylene types, amphoteric substances such as alkyl-betaine, imidazoline, glycine; cationic cleaning substances such as alkylammonium, pyridine, isoquinoline halides or sulphates or phosphates.

These cleaning substances are mixed with cooperating absorbing powders which can consist of: cellulose, modified amides, kaolin, bentonite, talc, silicates, silica, magnesium carbonates, magnesium hydroxide, attapulgite, montmorrillonite.

In order to allow the cleaning composition to be easily and quickly used it is possible to add to the above disclosed mixture disaggregating substances such as alginates, carraghenates, cellulose derivatives, gelatines, pectines, effervescent mixtures and the like, adapted to facilitate the releasing of the cleaning substance proper upon application to the skin.

The rubbery disaggregating substances must be added in a small amount so as to prevent, as water is added, any gelling from occurring which would involve a delay in the water dissolution of the composition, with a consequent increase of the application time of the composition.

In fact the subject composition which, after application, must be washed away from the skin, must be able of quickly disaggregating and dispersing in water; the water absorbed amount, moreover, must be comparatively small, in order to afford the possibility of using in the composition a very small amount of foaming solvent substances.

In actual practice the mentioned cleaning composition tablet should not swell or form dense gels.

To the disclosed composition lubricating materials can also be added such as talc, magnesium stearate, stearic acid, glycole stearates, Carbowax, skimmed powder milk, silicones and benzoates.

Softening, antibacteria, sequestering, coloring and perfuming agents can also be added.

Exclusively by way of an example, there are indicated thereinbelow some formulations of the skin cleaning composition according to the invention, which should be taken as merely indicative but not limitative.

EXAMPLE 1

Tablets for Cleaning the Hand Skin

ALKYLETHER SULPHATE 10%
COLLOIDAL SILICA 1%
KAOLIN 20%
LACTOSE 30%
TALC 10%
MAGNESIUM STEARATE 0.5%
SORBITOL balance to 100
(tablets of 1 g)

EXAMPLE 2

Tablets for Cleaning the Face

ALKYL GLYCINE 8%
ALKYL BETAINE 3%
STARCH 5%
BENTONITE 20%
POLYGLYCOL 6000 5%
SKIMMED POWDER MILK balance to 100
(tablets of 0.7 g)

EXAMPLE 3

Tablets for Cleaning the Body (for Shower)

ALKYL SULPHATE 4%
ALKYL IMIDAZOLINE 4%
COCONUT ALKYLAMIDE 2%
CARBOXYMETHYLCELLULOSE 2%
POWDER CELLULOSE 15%
WHITE KAOLIN 10%
CALCIUM PHOSPHATE 10%
SODIUM BENZOATE 3%
MANNITOL 20%
SACCHAROSE balance to 100
(Tablets of 6 g)

EXAMPLE 4

Multiple use Cleaning Tablets

SODIUM STEARATE AND PALMITATE 15%
POLYETHYLENEGLYCOLE STEARATE 5%
COLLOIDAL SILICA 2%
STEARIC ACID IN POWDER 1%
POTATO STARCH 10%
TALC 10%
SODIUM CHLORIDE 5%
GUAR GUM 2%
LACTOSE balance to 100
(Tablets from 1 to 10 g)

EXAMPLE 5

Foam Bath Tablets

ALKYLETHER SULPHATES 20%
ACYL GLUTAMATES 10%
MAIS STARCH 5%
OATS STARCH 5%
TALC 10%
GLUCOSE balance to 100
(tablets from 10 to 50 g)

EXAMPLE 6

Tablets for Cleaning the Body Bottom

ALKYLAMIDE SULPHATE 5%
COCONUT ALKYLAMIDE 3%
ALKYLAMIDEBETAINE 3%
ATTAPULGITE 10%
MAGNESIUM TRISILICATE 10%
MALTODEXTRINS 15%
MAGNESIUM STEARATE 0.5%
MANNITOL balance to 100
(Tablets of 1 g)

EXAMPLE 7

Shaving Foam Tablets

ALKALY SOAPS 10%
CARRAGEN 2%
TALC 10%
SACCHAROSE ESTERS 1%
BENTONITE 10%
LACTOSE balance to 100
(Tablets of 0.5%)

EXAMPLE 8

Shampoo Tablets

ALKYLSULPHATES 5%
SODIUM DIOCTYLSULPHOSUCCINATE 3%
LIPOPROTEINS 2%
MAGNESIUM CARBONATE 5%
POLYGLYCOLE 4000 6%
SODIUM CASEINATE 5%
COLLOIDAL SILICA 1%
KAOLIN 10%
LACTOSE balance to 100
(Tablets of 2 g)

EXAMPLE 9

Effervescent Cleaning Tablets

ALKYLETHER SULPHATES 5%
ALKYLAMIDOCARBOXYLATES 3%
DIALKYLAMIDEOXYDE 2%
TALC 10%
VEEGUM 20%
MICROGRANULAR CELLULOSE 10%
SODIUM BICARBONATE 10%
TARTARIC ACID 11.5%
LACTOSE balance to 100
(Tablets from 1 to 10 g)

EXAMPLE 10

Tablets with Quaternaries

ALKYLAMMONIUM HALIDES 1%

ISOQUINOLINE SACCHARINATES 2%
POLYOXYETHYLENESORBITANMONOLAURATE 3%
TALC 10%
ATTAPULGITE 10%
MALTODEXTRINS 20%
LACTOSE balance to 100
(tablets of 0.5 to 5 g)

The above disclosed compositions completely solve the problem of the personal cleaning, since they provide a tablet product which can be made as a single dose product and has very high cleaning properties, even in very samll doses.

Another important advantage of the invention is that the inventive tablets can be quickly and easily filled in dispensers.

While the invention has been disclosed and illustrated with reference to a preferred embodiment thereof, it should be apparent that the disclosed embodiment is susceptible to several modifications and variations all of which will come within the spirit and scope of the appended claims.

I claim:

1. A moisture free skin-cleaning composition in tablet form comprising a skin cleaning powder and at least one absorbing powder miscible with said skin cleaning powder, said skin cleaning powder being included in said composition in an amount from 1 to 20% by weight and selected from the group consisting of alkyl sulfates, alkylether sulfates, non-ionic soaps of alkylamide or polyoxyethylene, amphoteric compounds selected from the group consisting of alkylammonium pyridine, isoquinoline halides, sulfates and phosphates; said absorbing powder being included in said composition in an amount from 1 to 20% by weight and being selected from the group consisting of cellulose, modified starches, kaolin, bentonite, talc, silicates, silica, magnesium carbonates, magnesium hydroxide, attapulgite, montmorrillonite and mixtures thereof; said composition further comprising a lubricating material in an amount from 0.5 to 10% by weight and being selected from the group consisting of talc, magnesium stearate, stearic acid, glycol stearate, skimmed milk powder, silicones and benzoates; said composition further comprising a disaggregating substance in an amount from 1 to 10% by weight so as not to form gels with water, said disaggregating substance being selected from the group consisting of alginates, carrageen, cellulose derivatives, gelatins, pectins and effervescent mixtures.

* * * * *